United States Patent [19]

Pletka et al.

[11] 3,997,581
[45] Dec. 14, 1976

[54] PROCESS FOR THE PRODUCTION OF SULFUR CONTAINING ORGANOSILICON COMPOUNDS

[75] Inventors: Hans-Dieter Pletka, Hanau; Rudolf Michel, Freigericht, both of Germany

[73] Assignee: Deutsche Gold- und Silber-Scheideanstalt vormals Roessler, Frankfurt, Germany

[22] Filed: Jan. 31, 1975

[21] Appl. No.: 546,084

[30] Foreign Application Priority Data

Feb. 4, 1974 Germany .................. 2405758

[52] U.S. Cl. ............. 260/448.8 R; 260/448.2 E; 260/448.2 N
[51] Int. Cl.² ............ C07F 7/10; C07F 7/18
[58] Field of Search ........... 260/448.2 N, 448.8 R, 260/448.2 E

[56] References Cited
FOREIGN PATENTS OR APPLICATIONS 2,084,799  11/1971  France ............ 260/448.8 R UX

*Primary Examiner*—Paul F. Shaver
*Attorney, Agent, or Firm*—Cushman, Darby & Cushman

[57] ABSTRACT

Compounds are prepared having the formula $$Z-Alk-S_x-Alk\ Z \qquad I$$

wherein Z is

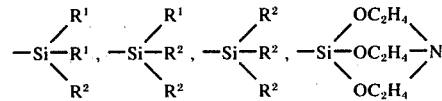

where
R¹ is an alkyl group of 1 to 4 carbon atoms, a cycloalkyl group having 5 to 8 carbon atoms or phenyl,
R² is an alkoxy group of 1 to 8 carbon atoms, a cycloalkoxy group of 5 to 8 carbon atoms or phenoxy,
Alk is a divalent hydrocarbon chain of 1 to 10 carbon atoms which can be interrupted with one or two —O—, —S— or —NH group, and
X is a number of 2 to 6 by reacting a compound having the formula II. Z—Alk—SH with sulfur. Some of the compounds are novel and some are old, e.g., in Meyer-Simon U.S. Pat. No. 3,842,111. The compounds are useful as bonding agents in sulfur vulcanizable rubbers.

14 Claims, No Drawings

PROCESS FOR THE PRODUCTION OF SULFUR CONTAINING ORGANOSILICON COMPOUNDS

This invention relates to a new, simple and reliable process for the production of organosilicon compounds some of which are known per se and others of which are novel in substantially quantitative yields from readily available starting materials. The process according to the invention comprises producing sulfur containing organo silicon compounds corresponding to the formula $$Z\text{—Alk—}S_x\text{—Alk—}Z \qquad (I)$$

in which Z is

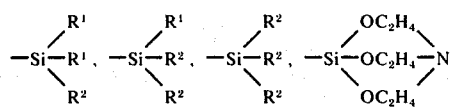

in which
R[1] is an alkyl group with a linear or branched chain containing 1 to 4 carbon atoms, a cycloalkyl radical with 5 to 8 carbon atoms or the phenyl radical and R[2] represents an alkoxy group with a linear or branched carbon chain with 1 to 8 carbon atoms, the methoxyethoxy group, a cycloalkoxy group with 5 to 8 carbon atoms or the phenoxy group, each R[1] and R[2] can be the same or different, Alk represents a divalent hydrocarbon radical with a linear or branched carbon chain with 1 to 10 carbon atoms, e.g., alkylene, which may optionally be interrupted once or twice by —O—, —S— or —NH—, and X is a number from 2.0 to 6.0 by reacting a compound corresponding to the formula (II) Z—Alk—SH with elemental sulfur.

The elemental sulfur is most suitably used in finely divided form, for example in the form of sulfur powder. The reaction generally begins at temperatures as low as room temperature (about 20° C.) after the two reactants have been brought together. The reaction is best carried out either at elevated temperature or at an increasing temperature in order to shorten the reaction time. The temperature is selected in dependence upon the type of mercapto compound used and may readily be determined and optimized by experiment. In general, the reaction temperature is in the range from about 10° to 250° C and more especially in the range from 20° to 200° C. It can be of advantage to carry out the reaction according to the invention in an organic solvent or solvent mixture. It is preferred to use polar solvents such as, for example, alcohols, e.g., alkanols such as methyl alcohol, ethyl alcohol, propyl alcohol, isopropyl alcohol, butyl alcohol, amyl alcohol and the like, also dimethyl formamide and ethers such as, especially cyclic ethers, for example, tetrahydrofuran, dioxan and the like. It is also possible to use acetone and aromatic hydrocarbons such as, for example, benzene, toluene, xylene and the like, as well as halogenated hydrocarbons such as, for example, carbon tetrachloride, trichloroethylene, chloroform, etc.

The process according to the invention takes place almost completely and also relatively quickly in the absence of a catalyst.

The process according to the invention is preferably carried out in the absence of air and/or moisture (water) in order to avoid side reactions. The reaction may be carried out, for example, in a dry inert gas, such as nitrogen or a noble gas, e.g. argon. However, it is also suitable to carry out the reaction under reduced pressure, although the application of slightly elevated pressure is also possible. The starting compounds used for the process according to the invention are the compounds corresponding to general formula (II) above, preferably those where Alk is a saturated hydrocarbon group, e.g., an alkylene group, with 2 to 8 and preferably with 2 to 4 carbon atoms and with 2 free, single valencies on two separate carbon atoms, and Z represents the group

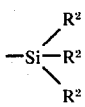

in which R[2] is an alkoxy group with 1 to 4 carbon atoms.

In the silane or silatrane group Z of formulae I and II, R[1] may be present either once or twice. As an alkyl group, R[1] is, for example, methyl, ethyl, i-propyl (i = iso), n-propyl, i-butyl, n-butyl, cyclopentyl, cyclohexyl, cycloheptyl, cyclooctyl, methyl cylcopentyl, dimethyl cyclopentyl, methyl cyclohexyl or dimethyl cyclohexyl and phenyl. By contrast, R[2] must be present once, twice or three times and represents an alkyl group attached to silicon through oxygen, and is preferably methoxy or ethoxy, but also can be i-propoxy, n-propoxy, n-butoxy, i-butoxy, 2-methyl butoxy, 3-methyl butoxy, n-pentoxy, n-hexoxy, 2-methyl pentoxy, 3-methyl pentoxy, 2,2-dimethyl butoxy, 2,3-dimethyl butoxy, n-heptoxy, 2-methyl hexoxy, 3-methyl hexoxy, 2,2dimethyl pentoxy, 3,3-dimethyl pentoxy, 2,3,3-trimethyl butoxy, etc., n-octoxy, i-octoxy, (2,4,4-trimethyl pentoxy), cyclopentoxy, cyclohexoxy, cycloheptoxy, cyclooctoxy, 2- or 3-methyl cyclopentoxy, 2-, 3- or 4-methyl cyclohexoxy, 3,4-dimethyl cyclopentoxy, 2,4-dimethyl cyclohexoxy, phenoxy or 2-methoxy-ethoxy.

In general formulae I and II, Alk represent methylene and, preferably, ethylene, i-propylene, n-propylene, i-butylene or n-butylene, but also can be n-pentylene 2methyl butylene, 3-methyl butylene, n-hexylene, 2-methyl pentylene, 3-methyl pentylene, 2,2-dimethyl butylene, 2,3-dimethyl butylene, n- and i-heptylene, octylene, nonylene or decylene. Alk can also have the following meanings: —CH$_2$—S—CH$_2$—; —CH$_2$—O—CH$_2$—; —CH$_2$—NH—CH$_2$—; —CH$_2$—S—CH$_2$CH$_2$—; —CH$_2$—O—CH$_2$CH$_2$—; —CH$_2$—NH—CH$_2$CH$_2$—; —CH$_2$CH$_2$—s—CH$_2$CH$_2$—; —CH$_2$CH$_2$—O—CH$_2$CH$_2$Ch$_2$——CH$_2$CH$_2$—NH—CH$_2$CH$_2$—; —CH$_2$—S—CH$_2$—S—CH$_2$—; —CH$_2$—O—CH$_2$O—CH$_2$—; —CH$_2$—NH—CH$_2$—NH—CH$_2$—; —CH$_2$—S—CH$_2$CH$_2$—S—CH$_2$—; —CH$_2$—O—CH$_2$CH$_2$—O—CH$_2$—; —CH$_2$—NH—CH$_2$CH$_2$—NH—CH$_2$—; —CH$_2$CH$_2$—S—CH$_2$—S—CH$_2$CH$_2$—; —CH$_2$CH$_2$—O—CH$_2$—O—CH$_2$CH$_2$—; —CH$_2$CH$_2$—NH—CH$_2$—NH—CH$_2$—CH$_2$—; —CH$_2$CH$_2$—S—CH$_2$CH$_2$—S—CH$_2$CH$_2$—; —CH$_2$CH$_2$O—CH$_2$CH$_2$—; —CH$_2$CH$_2$—NH—CH$_2$CH$_2$NH—CH$_2$CH$_2$—; —(CH$_2$-

)₃—S—(CH₂)₃—S—(CH₂)₃——; —(CH₂)₃—O—(CH₂-)₃—O—(CH₂)₃—; —; —(CH₂)₃—NH—(CH₂)₃—NH—(CH₂)₃—; —CH₂CH(CH₃) —O—CH₂CH(CH₃)—O—CH₂CH(CH₃)—; —(CH₂)₄—NH—(CH₂)₄—; —(CH₂)₄—O(CH₂)₄—; —(CH₂)₂CH(CH₃)—S—CH(CH₃) (CH₂)₂—; —(CH₂)₅—O(CH₂)₅; —(CH₂)₅—S—(CH₂)₅; —(CH₂)₅—NH—(CH₂)₅— .

Examples of compounds within Formula II are: trimethoxysilylethyl mercaptan, trimethoxysilylethyl mercaptan, trimethoxysilylpropyl mercaptan, trimethoxysilyl-i-propyl mercaptan, trimethoxysilylbutyl mercaptan, trimethoxysilylpentyl mercaptan, trimethoxysilylhexyl mercaptan, trimethoxysilylmethylhexyl mercaptan, trimethoxysilylheptyl mercaptan, trimethoxysilyloctyl mercaptan, trimethoxysilyldecyl mercaptan, triethoxysilylmethyl mercaptan, triethoxysilylethyl mercaptan, triethoxysilylpropyl mercaptan, triethoxysilylbutyl mercaptan, triethoxysilylamyl mercaptan, triethoxysilylhexyl mercaptan, triethoxysilylheptyl mercaptan, triethoxysilyloctyl mercaptan, triethoxysilylnonyl mercaptan, triethoxysilyldecyl mercaptan, tripropoxysilylethyl mercaptan, tripropoxysilylpropyl mercaptan, tributoxysilylethyl mercaptan, tributoxysilylpropyl mercaptan, tributoxysilylpropyl mercaptan, triisobutoxysilylpropyl mercaptan, tricyclopentoxysilylpropyl mercaptan, tricyclohexoxysilylpropyl mercaptan, tricyclooctoxysilylethyl mercaptan, tri-2-methylcyclohexoxysilylethyl mercaptan, triphenoxysilylethyl mercaptan, triphenoxysilylpropyl mercaptan, triethoxysilyl-2-methylpropyl mercaptan, triethoxysilylethoxyethyl mercaptan, trimethoxysilylmethoxymethyl mercaptan, triethoxysilylethylthioethyl mercaptan, trimethoxysilylemethylthioethyl mercaptan, triethoxysilylmethoxymethoxymethyl mercaptan, trimethoxysilylmethylthioethylthiomethyl mercaptan, trimethoxysilylmethylaminomethyliminomethyl mercaptan, triethoxysilylethyliminomethyliminoethyl mercaptan, triethoxysilylpropoxypropyl mercaptan, triethoxysilylamyloxyamyl mercaptan, dimethoxyethoxysilylpropyl mercaptan, triamyloxysilylethyl mercaptan, trihexoxysilylpropyl mercaptan, trioctoxysilylpropyl mercaptan, methyldimethoxysilylethyl mercaptan, dimethyl methoxysilylpropyl mercaptan, ethyl diethoxysilylbutyl mercaptan, butyl dimethoxysilylethyl mercaptan, dibutyl propoxysilylamyl mercaptan, tris-(2methoxyethoxy)-silylethyl mercaptan, tris-(2-methoxyethoxy)-silylpropyl mercaptan, tris-(2-methoxyethoxyl)-silylmethylpropyl mercaptan, tris-(2-methoxyethoxy)-silylbutyl mercaptan and bis-(2methoxyethoxy) ethoxysilylpropyl mercaptan.

The new reaction takes place in accordance with the following equation:

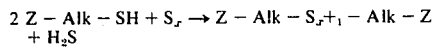

The yield is substantially quantitative providing the sulphur is used in a suitable, generally molar, quantity. A molar ratio of Z — Alk — SH to sulfur of 1:0.5 to 1:2.5 is preferred. As a rule most of the hydrogen sulphide formed escapes. Any residue of hydrogen sulphide left in the liquid reaction product can be removed, for example, by applying a vacuum, as can any residue of the solvent which, basically, is removed by distillation.

Most of the polysulphidic silanes corresponding to formula 1 above are known from German Offenlegungsschrift No. 2,141,160 and Meyer-Simon U.S. Pat. No. 3,842,111. However, they are of course produced by different reactions. Another method for their production from that in German Offenlegungsschrift No. 2,141,160 is described in German Offenlegungsschrift No. 2,141,159 and also in the Meyer-Simon Pat. No. 3,842,111. The entire disclosure of Meyer-Simon is hereby incorporated by reference and relied upon. The process according to the invention is surprisingly simple by comparison with those art reactions both in regard to the way in which it is carried out and also in the substantially quantitative yield it provides. Mixture of silanes, i.e., di-, tri-, tetra-, penta- and/or hexa-sulphides, may possibly be formed in various ratios in regard to the number of sulphur atoms.

The outlay for apparatus in the process according to the new process is minimal. For the reasons discussed above, the process according to the invention is also very economical.

Some of the compounds obtainable in accordance with the invention are new. These compounds, which are being claimed, are organo silicon compounds corresponding to the formula $$Z_1 - Alk - S_x - Alk - Z_1 \qquad (III)$$

in which $Z_1$ is

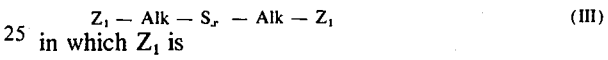

in which
$R^1$ is a cycloalkyl radical with 5 to 8 carbon atoms, and
$R^2$ is an alkoxy group with a linear or branched carbon chain containing 1 to 8 carbon atoms, the methoxyethoxy group, a cycloalkoxy group with 5 to 8 carbon atoms or the phenoxy group, each $R^1$ and $R^2$ optionally being the same or different,
Alk is a divalent hydrocarbon radical, e.g., alkylene with a linear or branched carbon chain of 1 to 10 carbon atoms which may optionally be interrupted once or twice by —O—, —S— or —NH—, and
$x$ is a number from 2.0 to 6.0, or compounds of the formula IV Z —Alk'—S$_x$—Alk—Z in which Z represents the groups

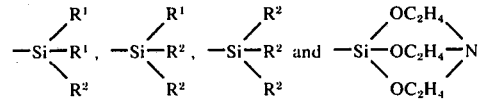

in which
$R^1$ is an alkyl group with a linear or branched chain of 1 to 4 carbon atoms, a cycloalkyl radical with 5 to 8 carbon atoms, or the phenyl radical and
$R^2$ is an alkoxy group with a linear or branched carbon chain of 1 to 8 carbon atoms, the methoxyethoxy group, a cycloalkoxy group with 5 to 8 carbon atoms or the phenoxy group, each $R^1$ and $R^2$ optionally being the same or different,
Alk' is a divalent hydrocarbon radical with a linear or branched carbon chain having 1 to 10 carbon atoms which is interrupted once or twice by —O—, —S— or —NH—, and
$x$ is a number from 2.0 to 6.0.

Most of the compounds obtained in accordance with the invention are liquid at room termperature and cannot be distilled without decomposing. However, they generally do not have to be purified for use of the reaction products.

The following are examples of compounds obtainable in accordance with the invention: 3,3'-bis-(trimethoxysilylpropyl)-disulphide, 3,3'-bis-(triethoxysilylpropyl)-tetrasulfide, 3,3'-bis-(trimethoxysilylproply)-tetrasulfide, 3,3'-bis-(triethoxysilylpropyl)-disulfide, 2,2'-bis-(triethoxysilylethyl)-tetrasulphide, 3,3'-bis-(trimethoxysilylpropyl)-trisulphide, 3,3'-bis-(triethoxysilylpropyl)-trisulfide, 3,3'-bis-(tri-n-butoxysilylpropyl)-disulphide, 3,3'-bis-(trimethoxysilylpropyl)-hexasulphide, 3,3'-bis-(trioctoxysilypropyl)-tetrasulphide, 3,3'-bis-(trihexoxysilylpropyl)-dilsulfide, 3,3'-bis-(tri-2''-ethylhexoxysilylpropyl)-trisulfide, 3,3'-bis-(triisooctoxysilylpropyl)-tetrasulphide, 3,3'-bis-(tri-t.-butoxysilylpropyl)-disulphide, 2,2'-bis-(methoxydiethoxysilylethyl)-tetrasulphide 2,2'-bis-(tri-n-propoxysilylethyl)-pentasulphide, 3,3'-bis-tricyclohexoxysilylpropyl)-tetrasulphide, 3,3'-bis-(tricyclopentoxyslypropyl)-trisulphide, 2,2'-bis-(tri-2''-methylcyclohexoxysilylethyl)-tetrasulphide, bis-(trimethoxysilylmethyl)-tetrasulphide, 3,3'-bis-(diethoxymethylsilylpropyl)-tetrasulphide, 2,2'-bis-(diethoxyphenylsilylethyl)-disulphide, 2,2'-bis-(ethoxydimethyl silylethyl)-trisulphide, 2,2'-bis-(di-sec.-butyloxysilylethyl-trisulphide, 3,3'-bis-(dioctyloxyoctylsilylpropyl)-tetrasulphide, 2,2'-bis-(dihexyloxyphenylsilylethyl)-hexasulphide, 3,3'-bis-(ethyldipropoxysilylpropyl)-tetrasulphide, 3,methoxyethoxy-propoxysilyl-3'-diethoxybutoxysilylpropyltetrasulphide, 2,2'-bis-(dimethylmethoxysilylethyl)-disulphide, 2,2'-bis-(dimethyl-sec.-butoxysilylethyl)-trisulphide, 3,3'-bis-(methyl-butylethoxysilylpropyl)-tetrasulphide, 3,3'-bis-(di-t.-butylmethoxysilylpropyl)-tetrasulphide 4,4'-bis-(phenylethylethoxysilyl)-n-butyl)-trisulphide, 3,3'-bis-(diphenyl-isopropoxy silylpropyl)-tetrasulphide, 3,3'-bis-(diphenylcyclohexoxysilylpropyl)-disulphide, 4,4'-bis-(dimethylethoxysilyl-i-pentyl)-tetrasulphide, 3,3'-bis-(methyl-dimethoxysilyl-i-butyl)-trisulphide, 5,5'-bis-(methylethoxypropoxysilyl-n-pentyl)-tetrasulphide, 2,2'-bis-(diethylethoxysilyl-i-propyl)-tetra-sulphide, 3,3'-bis-(ethyl-di-sec.-butoxysilylpropyl)-disulphide, 3,3'-bis-(propyl-diethoxysilylpropyl)-hexasulphide, 3,3'-bis-(butyldiethoxysilylpropyl)-trisulphide, 3,3'-bis-(phenyldiethoxysilylpropyl)-tetrasulphide, 3phenylethoxybutoxysilyl3'-triethoxysilylpropyl-tetrasulphide, 4,4'-bis-(triethoxysilyl-n-butyl)-tetrasulphide, 6,6'-bis-(triethoxysilyl-n-hexyl)-tetrasulphide, 10,10'-bis-(triisopropoxysilyl-n-decyl)-disulphide, 8,8'-bis-(triethoxysilyloctyl)-tetrasulphide, 10,10'-bis-(tripropoxysilyldecyl)-tetrasulphide, 4,4'-bis-trimethoxysilyl-n-butyl)-tetrasulphide, 6,6'-bis-(trimethoxyslylhexyl)-tetrasulphide, 5,5'-bis-(dimethoxyethylsilylpentyl)-trisulphide, 3,3'-bis-(triethoxysilyl-2methylpropyl)-trisulphide, 3,3'-bis-(diethoxyphenylsilyl-3methylpropyl)-disulphide 3,3'-bis-(diethoxycyclopentylsilylpropyl)disulphide, -bis-(propoxycyclohexylsilylethyl)disulphide 3,3'-bis(dimethoxycyclohexylsilylpropyl)trisulphide, 3,3-bis(dimethoxycyclooctylsilylpropyl)tetrasulphide, 2,2-bis(-dibutoxymethylcyclohexylsilylethyl)hexasulphide, 3,3'-bis(dioctoxycyclopentylsilylpropyl)tetrasulphide, 3,3'-bis(ethoxydicyclopentylsilylpropyl)trisulphide, 2,2'-bis(methoxycyclopentylsilylethyl)tetrasulphide, 2,2'-bis(propoxycyclohexylisilylethyl)disulphide 2,2'-bis[tris-2-methoxyethoxy)-silylethyl]3,3'-bis[tris-(2-methoxyethoxy)-silylpropyl]tetrasulphide, 4,4'-bis[-tris-(2-methoxyethoxy)silylbutyl]trisulphide, 3,3'-bis[-tris-(2-methoxyethoxy)-silylisobutyl]-trisulphide, 3,3'-bis[tris(2-methoxyethoxy)-silylisobutyl]2,2'-bis[tris-(2-methoxyethoxy)-silylethyl]3,3'-bis[tris-(2-methoxyethoxy)-silylpropyl]disulphide, 2,2'-bis[tris-(2-methoxyethoxy)-silylethyl]3,3'-bis[tris-(2-methoxyethoxy)-silylpropyl]trisulphide, 3,3 -bis[tris-(2-methoxyethoxy)-silylisobutyl]disulphide, 3,3'-bis(phenoxydicyclohexylslylpropyl)disulphide, 3,3'-bis(diphenoxycyclopentylsilylpropyl)trisulphide, 3,3'-bis(dicyclopentoxycyclohexylisilylpropyl)disulphide,

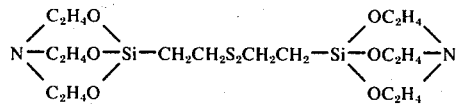

and the corresponding compounds where there are 3, 4, 5 or 6 atoms of sulfur as well as the compounds where Alk is propylene, butylene rather than ethylene, bis(triethoxysilylethoxyethyl)disulphide, bis(trimethoxyslylmethoxymethyl) trisulphide, bis(triethoxysilylethy)-thioethyl)tetra sulphide, bis(trimethoxysilylmethylthioethyl)trisulphide, bis(triethoxsililymethoxy-methoxymethyl)disulphide, bis(trimethoxysilylmethyl- bis(trimethoxysilyl-methyliminomethyl)disulphide, bis(triethoxysilylethyliminomethyliminoethyl)-trisulphide, bis(triethoxysilylpropoxypropyl)tetrasulphide, bis(triethoxysilylamyloxyamyl)disulphide, bis(-dimethoxyethoxysilylpropyl)trisulphide, 2,2'bis(-triamyloxysilylethyl)tetrasulphide, 3,3'-bis(trihexoxysilyl-propyl)disulphide, It is already known that alkyl and cycloalkyl mercaptans dissolved in solvents can be oxidized with sulphur in the presence of basic catalysts such as amines, for example n-propyl amine, or alkali metal hydroxides (J. Org. Chem. 31 (2), 601–602 (1966), J. Org. Chem. 32 (12), 3833–3836 (1967) and U.S. Pat. No. 3,340,324). These reactions yield alkyl di-, tri- and tetra-sulphides and mixtures thereof.

Unless otherwise indicated all parts and percentages are by weight.

EXAMPLE 1

2 moles of 3-mercaptopropyl trimethoxysilane corresponding to the formula $HS-(CH_2)_3-Si(OCH_3)_3$

| Analysis: | % C | % H | % Si | % S |
|---|---|---|---|---|
| Found: | 36.7 | 8.25 | 14.28 | 16.30 |
| Calculated: | 36.74 | 8.20 | 14.24 | 16.37 | and 2 moles of sulphur are introduced into and heated while stirring in a three-necked flask equipped with a stirrer, internal thermometer and nitrogen dip frit for removing hydrogen sulphide. The first traces of $H_2S$ are given off at slightly elevated temperature, although the main reaction takes place at approximately 120° C. After 1 hour, the reaction temperature has reached 150° C and the reaction is over. The compound is freed from residual, dissolved hydrogen sulphide by applying an adequate reduced pressure. According to combusion analysis, bis-(3-trimethoxysilylpropyl)-trisulphide is obtained in a substantially quantitative yield.

| Analysis:   | % C   | % H  | % Si  | % S   |
|-------------|-------|------|-------|-------|
| Found:      | 34.07 | 7.10 | 13.37 | 23.43 |
| Calculated: | 34.12 | 7.11 | 13.29 | 22.76 |

EXAMPLE 2

The procedure is as in Example 1, except that 1.5 moles of sulphur are used per mole of the mercaptosilane. bis(3-trimethoxysilylpropyl)-tetrasulphide is obtained:

| Analysis:   | % C   | % H  | % Si  | % S   |
|-------------|-------|------|-------|-------|
| Found:      | 30.78 | 6.51 | 12.30 | 28.2  |
| Calculated: | 31.7  | 6.60 | 12.34 | 28.21 |

EXAMPLE 3

The procedure is again as in Example 1, except that 0.5 mole of sulphur are used per mole of mercaptosilane. Bis-(3-trimethoxysilylpropyl)-disulphide is obtained:

| Analysis:   | % C   | % H  | % Si  | % S   |
|-------------|-------|------|-------|-------|
| Found:      | 36.23 | 7.70 | 14.35 | 16.28 |
| Calculated: | 36.89 | 7.74 | 14.38 | 16.41 |

EXAMPLE 4

2 moles of 3-mercaptopropyl-triethoxysilane of the formula $HS-(CH_2)_3-Si(O_2H_5)_3$

| Analysis:   | % C   | % H  | % Si  | % S   |
|-------------|-------|------|-------|-------|
| Found:      | 44.97 | 8.71 | 11.80 | 13.29 |
| Calculated: | 45.53 | 8.91 | 11.83 | 13.50 | and three moles of sulphur are introduced into the apparatus described in Example 1. When the reaction mixture is stirred, the evolution of H₂S begins immediately, reaching its maximum between 30° and 70 ° C. After 1 hour, by which time the temperature has reached approximately 100° C, the reaction is over, bis-(3-triethoxysilylpropyl)-tetrasulphide being obtained in a substantially quantitative yield.

| Analysis:   | % C   | % H  | % Si  | % S   |
|-------------|-------|------|-------|-------|
| Found:      | 40.01 | 7.80 | 10.28 | 25.81 |
| Calculated: | 40.11 | 7.84 | 10.42 | 23.79 |

EXAMPLE 5

2 moles of 3-mercaptopropyl-triethoxysilane are dissolved in 500 ml of ethyl alcohol in the flask of the apparatus described in Example 1, followed by the addition of 3 moles of sulphur. The reaction mixture is heated, the first significant signs of any gas being given off being observed at as low as 50°C. The main reaction takes place between 60°C and 70°C. After boiling under reflux for 1.5 hours, the reaction is over, bis-(3-triethoxysilylpropyl)-tetrasulphide being obtained in a substantially quantitative yield, as confirmed by analysis, following removal of the ethyl alcohol, for example in vacuo.

EXAMPLE 6

2 moles of 3-mercaptopropyl-tri-n-butoxysilane corresponding to the formula $HS-(CH_2)_3 Si (O-n-C_4H_9)_3$

| Analysis:   | % C   | % H   | % Si | % S  |
|-------------|-------|-------|------|------|
| Found:      | 54.21 | 9.91  | 8.64 | 9.79 |
| Calculated: | 55.85 | 10.62 | 8.70 | 9.93 | and 3 moles of sulphur are introduced into the apparatus described in Example 1 and heated. The evolution of gas begins at around 160° C. The reaction is over after about 2 hours by which time the temperature has reached 175° C. Bis-(3-tri-n-butoxysilylpropyl)-tetrasulphide is obtained in an almost quantitative yield.

| Analysis:   | % C   | % H  | % Si | % S   |
|-------------|-------|------|------|-------|
| Found:      | 50.74 | 9.21 | 7.82 | 17.94 |
| Calculated: | 51.31 | 9.42 | 7.90 | 18.12 |

EXAMPLE 7

2 moles of the (mixed)mercaptosilane

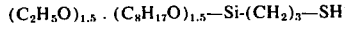

$(C_2H_5O)_{1.5} \cdot (C_8H_{17}O)_{1.5}-Si-(CH_2)_3-SH$

| Analysis:   | % C   | % H   | % Si | % S  |
|-------------|-------|-------|------|------|
| Found:      | 58.97 | 10.88 | 7.68 | 8.71 |
| Calculated: | 59.33 | 11.06 | 7.70 | 8.79 | and 3 moles of sulphur are introduced into the apparatus described in Example 1. The reaction begins distinctly at a temperature of around 100° C with stirring. The reaction is over heating for about 2 hours to a temperature of approximately 130° C. The corresponding mixed bis-(3-alkoxysilylpropyl)-tetrasulphide, (in regard to the alkoxy groups) is obtained in a substantially quantitative yield.

| Analysis:   | % C   | % H  | % Si | % S   |
|-------------|-------|------|------|-------|
| Found:      | 53.72 | 9.81 | 6.91 | 15.92 |
| Calculated: | 54.81 | 9.92 | 7.04 | 16.20 |

EXAMPLE 8

The procedure is as in Example 1 using 3-mercaptopropyl-triethoxysilane. 0.5 mole of sulphur are used per mole of that mercaptosilane. Hydrogen sulphide begins to be given off immediately after the beginning of stirring. Most of the hydrogen sulphide is given off between about 30° and 70° C. The reaction is over after 1 hour by which time the temperature has reached approximately 100° C. Bis-(3-triethoxylsilylpropyl)-disulphide disulphide is obtained in a substantially quantitive yield:

| Analysis:   | % C   | % H  | % Si  | % S   |
|-------------|-------|------|-------|-------|
| Found:      | 45.60 | 8.90 | 11.62 | 12.97 |
| Calculated: | 45.63 | 8.90 | 11.78 | 13.40 |

EXAMPLE 9

The reaction of 2 moles of 3-mercapto-i-butyl triethoxy silane corresponding to the formula

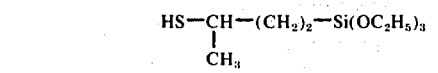

| Analysis: | % C | % H | % Si | % S |
|---|---|---|---|---|
| Found: | 47.38 | 9.94 | 11.07 | 12.65 |
| Calculated: | 47.36 | 9.97 | 11.0 | 12.68 | and 3 moles of sulphur under the same conditions as in Example 1 yields bis-(3-triethoxysilyl-i-butyl)-tetrasulphide. silane corresponding to the formula

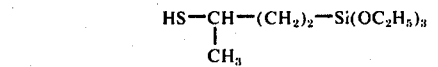

| Analysis: | % C | % H | % Si | % S |
|---|---|---|---|---|
| Found: | 47.38 | 9.94 | 11.07 | 12.65 |
| Calculated: | 47.36 | 9.97 | 11.0 | 12.68 | and 3 moles of sulfer under the same conditions as in Example 1 yields bis-(3-triethoxysilyl-i-butyl)-tetrasulfide.

| Analysis: | % C | % H | % Si | % S |
|---|---|---|---|---|
| Found: | 41.87 | 8.03 | 9.84 | 21.98 |
| Calculated: | 42.40 | 8.12 | 9.90 | 22.62 |

EXAMPLE 10

4 moles of sulphur are added with stirring to 2 moles of 3-mercaptopropyl trimethoxysilane, followed by heating, in the apparatus and under the conditions described in Example 1. Bis-(3-trimethoxysilylpropyl)-pentasulphide with the following analysis is obtained:

| | % C | % H | % Si | % S |
|---|---|---|---|---|
| Found: | 29.03 | 6.18 | 11.47 | 33.27 |
| Calculated: | 29.61 | 6.21 | 11.53 | 32.95 |

The end products of the process according to the invention are useful intermediate products and may be used with particular advantage as rubber additives, for example in rubber mixtures containing silica-like pigments or fillers such as, for example, silicates, silicas themselves, silicate glass products or the like. They are useful as bonding agents for sulfur vulcanizable rubbers and all of the other uses disclosed in Meyer-Simon U.S. Pat. No. 3,842,111.

The process can comprise consist essentially of, or consist of the steps and materials set forth.

What is claimed is:

1. A process for the production of sulfur containing organo silicon compounds corresponding to the general formula

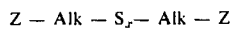

in which Z represents the group

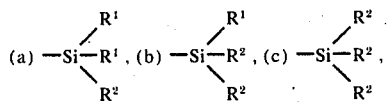

or

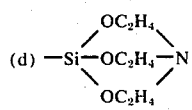

in which
R¹ is an alkyl group containing 1 to 4 carbon atoms, a cycloalkyl radical with 5 to 8 carbon atoms or the phenyl radical, and
R² represents an alkoxy group with a linear or branched carbon chain with 1 to 8 carbon atoms, the methoxyethoxy group, a cycloalkoxy group with 5 to 8 carbon atoms or the phenoxy group, each R¹ and R² optionally being the same or different,
Alk represents either a divalent hydrocarbon radical with 1 to 10 carbon atoms in the carbon chain or such a hydrocarbon radical interrupted once or twice by —O—, —S— or —NH—,
x is a number from 2.0 to 6.0, comprising reacting a compound corresponding to the general formula

with elemental sulfur.

2. A process according to claim 1 where Alk is alkylene of 1 to 10 carbon atoms.

3. A process as claimed in claim 2 wherein the reaction is carried out at elevated temperature with a molar ratio of Z — Alk — SH to sulfur of 1:0.5 to 1:2.5.

4. A process as claimed in claim 2 wherein the reaction is carried out in the presence of an organic solvent.

5. A process according to claim 2 carried out in the absence of a solvent.

6. A process as claimed in claim 2 wherein the reaction is carried out with a compound of formula II, in which Alk is an ethylene, n-propylene, i-propylene, n-butylene or i-butylene group and Z represents the group

in which R² is an alkoyxy group with 1 to 4 carbon atoms.

7. A procuess according to claim 1 wherein R¹ is alkyl of 1 to 4 carbon atoms or phenyl, R² is alkoxy of 1 to 8 carbon atoms or cycloalkoxy with 5 to 8 carbon atoms and Alk is a divalent hydrocarbon group of 1 to 10 carbon atoms and Z is (a), (b) or (c).

8. A process according to claim 7 wherein Alk is an alkylene group of 1 to 10 carbon atoms.

9. A process according to claim 8 wherein R¹ is alkyl of 1 to 4 carbon atoms and R² is alkoxy of 1 to 8 carbon atoms.

10. A process according to claim 9 wherein the molar ratio of Z—Alk—SH to sulfur is from 1:05 to 1:2.5.

11. A process according to claim 10 wherein Alk is alkylene of 2 to 3 carbon atoms.

12. A sulfur containing organosilicon compound corresponding to the general formula

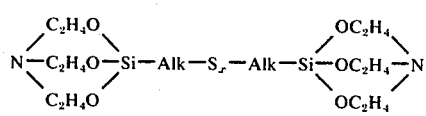

where Alk is a divalent hydrocarbon radical with 1 to 10 carbon atoms in the claim or a divalent hydrocarbon radical with 1 to 10 carbon atoms which is interrupted once or twice by —O—, —S— or —NH— and $x$ is a number from 2.0 to 6.0.

13. A compound claim to claim 12 wherein Alk is an alkylene group of 1 to 10 carbon atoms.

14. A compound according to claim 12 wherein Alk is a divalent hydrocarbon radical with 1 to 10 carbon atoms which is interrupted once or twice by —O—, —S— or —NH—.

* * * * *